(12) United States Patent
Karlinsey

(10) Patent No.: US 8,568,696 B2
(45) Date of Patent: Oct. 29, 2013

(54) GRINDING METHOD FOR THE MANIPULATION OR PRESERVATION OF CALCIUM PHOSPHATE HYBRID PROPERTIES

(75) Inventor: Robert L. Karlinsey, Indianapolis, IN (US)

(73) Assignee: Indiana Nanotech LLC, Indianapolis, IN (US)

( * ) Notice: Subject to any disclaimer, the term of this patent is extended or adjusted under 35 U.S.C. 154(b) by 1437 days.

(21) Appl. No.: 12/186,940

(22) Filed: Aug. 6, 2008

(65) Prior Publication Data

US 2010/0034756 A1 Feb. 11, 2010

(51) Int. Cl.
*A61K 9/50* (2006.01)
*C01F 11/00* (2006.01)
*A61K 9/16* (2006.01)
A61K 6/00 (2006.01)
C08K 3/32 (2006.01)

(52) U.S. Cl.
CPC .................. *A61K 9/16* (2013.01); *A61K 9/1611* (2013.01); *A61K 9/1617* (2013.01); *A61K 6/0052* (2013.01); *C01F 11/00* (2013.01); *C08K 2003/325* (2013.01)
USPC .................. 424/49; 424/52; 424/57; 424/489

(58) Field of Classification Search
USPC ......................................................... 424/52
See application file for complete search history.

(56) References Cited

U.S. PATENT DOCUMENTS

| 4,048,300 | A | * | 9/1977 | Tomlinson et al. | 424/52 |
| 5,993,786 | A | * | 11/1999 | Chow et al. | 424/49 |
| 2006/0115437 | A1 | * | 6/2006 | Hayman et al. | 424/53 |
| 2008/0187500 | A1 | * | 8/2008 | Karlinsey | 424/52 |

OTHER PUBLICATIONS

Arends et al., Interaction of Urea and Human Enamel, Caries Research, 1984, 18, pp. 1984.*
Ning et al., Effects of silica on the bioactivity of calcium phosphate composites in vitro, J. of Materials Science, 2005, 16, pp. 355-360.*
Shyrock, H., Tooth-Colored Restoratives, Chapter 2 Diagnosis, 2002, pp. 19-41.*

* cited by examiner

*Primary Examiner* — Frederick Krass
*Assistant Examiner* — Isaac Shomer
(74) *Attorney, Agent, or Firm* — Brannon Sowers & Cracraft PC

(57) ABSTRACT

A solid state method of encouraging the physical interfacing of an organic component to a substantially crystalline inorganic component, including adding predetermined amounts of a substantially crystalline inorganic precursor and a predetermined amount of an organic precursor to yield an admixture, maintaining the admixture in a substantially liquid-free environment, and impacting the precursors together with sufficient energy to fuse the precursors into hybrid compounds. The so-formed hybrid compounds substantially retain the long range crystalline order characteristics of the substantially crystalline inorganic precursor.

7 Claims, 3 Drawing Sheets

GRINDING METHOD FOR THE MANIPULATION OR PRESERVATION OF CALCIUM PHOSPHATE HYBRID PROPERTIES

CROSS-REFERENCE TO RELATED APPLICATIONS

This application is a continuation-in-part of and claims priority to co-pending utility patent application Ser. No. 12/210,137, filed Sep. 12, 2008; co-pending utility patent application Ser. No. 12/018,627, filed Jan. 23, 2008 and published as U.S. Pat. Pub. No. 2008/0187500; U.S. provisional patent application Ser. No. 60/888,354, filed February 6, 2007; U.S. provisional patent application Ser. No. 60/891,849, filed Feb. 27, 2007; and U.S. provisional patent application Ser. No. 60/941,095, filed May 31, 2007, each of which are incorporated herein in their entirety by reference.

TECHNICAL FIELD

The present novel technology relates generally to the field of chemical and composite synthesis, and, more particularly, to a method and system for manipulating or preserving properties of calcium phosphate materials.

BACKGROUND

Improving the health of mineralized tissue, including bone and teeth, by the delivery of minerals are important goals in the dental and orthopedic fields. In preventive dentistry, there is a strong desire to simultaneously deliver minerals, such as a calcium and fluoride, in an attempt to reduce dental wear and erosion, the formation of caries, and hypersensitivity. With respect to fluoride-based dental vehicles, such as toothpaste, conventional mineral treatments are only marginally effective in providing useful minerals. This is due in part to the undesirable interaction of calcium and fluoride, which can reduce vehicle efficacy. In orthopedics, implant coatings or pastes are desired to stimulate favorable biological responses and integration, but conventional means often illicit these responses too slowly.

Clearly then, there is a need for mineral delivery compounds that can aid in the reconstruction of weakened teeth and bones. The embodiments discussed herein, address these needs.

With respect to creating well-ordered materials spanning dimensions from nanometers to micrometers, typical synthetic methods may include quenching, annealing, compression, precipitation, and nucleation and growth reactions. While these methods each are characterized by their own advantages and disadvantages, there remains an overarching need for an economical and powerful method of creating mixed-phase materials manifesting ordered morphologies. Advantages of creating such a hybrid material may include, for instance, the ability to combine soft and hard components to produce a hybrid material that can be combined in the presence of other reagents in a medium without compromising either the integrity of the hybrid material or the reagents, while simultaneously improving the overall properties of the medium comprising all components. There exist technological challenges and opportunities in developing methods to create blended materials from individual starting materials manifesting unique chemical and physical properties without distorting specific properties of certain starting materials. Such a method, then, is highly desired and is the focus of the present novel technology.

Thus, there remains a need for a method of creating hybrid materials, where specific properties of the starting materials are left intact, in order to produce a hybrid material with properties designed for specific applications. The present novel technology addresses this need.

SUMMARY

The present novel technology relates to hybrid materials and a solid-state method for producing the same.

One object of the present novel technology is to provide an improved method for producing hybrid materials with preserved and modified properties. Further objects, features, and advantages will become apparent from a consideration of the following description and accompanying drawings.

One aspect of the presently novel technology relates to a combination of organic and inorganic systems in such a way as to readily avoid the complications of combining dissimilar reagents manifesting a wide range in chemical and physical properties. Such properties may include: 1) melting and softening points; 2) structural morphology and percent crystallinity; 3) elasticity and compressibility; 4) hydrophilicity and/or hydrophobicity; 5) bond strength, and 6) particle, cluster, or crystallite size.

The present novel technology further relates to a method for producing a thermodynamically and kinetically stable material that slowly releases ions and moieties when solvated due to the complex chemistry created during the milling process.

The present novel technology still further relates to the production of a hybrid material with preserved properties, such as morphology of the bulk component. The formation and/or retention of chemical and physical phases and structures facilitate and modulate interactions among the hybrid material and other components when added to condensed phases, including fluoride-containing or fluoride-free dental vehicles.

DESCRIPTION OF THE PREFERRED EMBODIMENT

Figure 1:
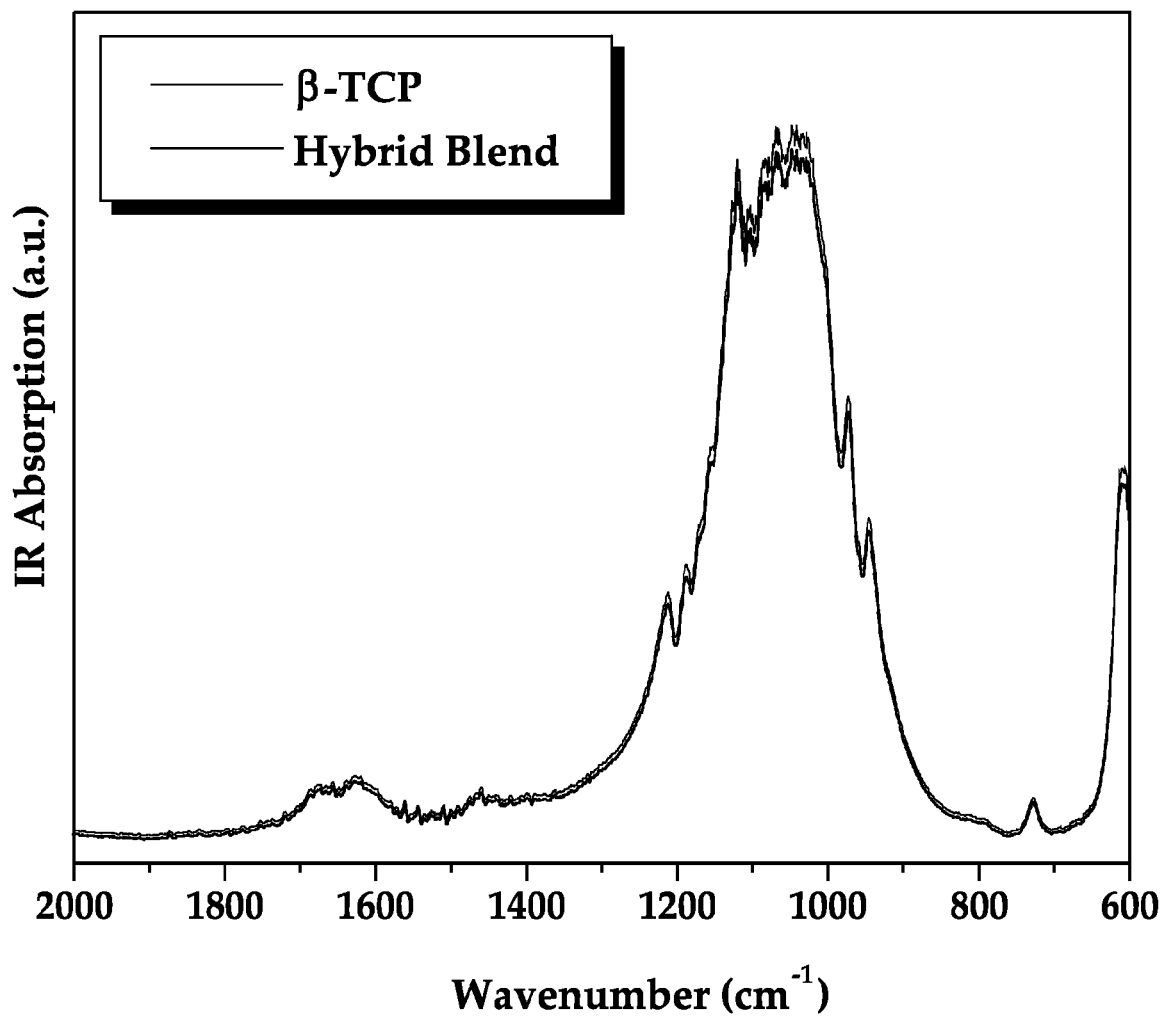
FIG. 1 graphically illustrates infrared spectra in the characteristic vibrational range of orthophosphate (2000 to 600 $cm^{-1}$) for the pure component ($\beta$-TCP) and the TCP-Silica-Carbamide system FIG. 2 graphically illustrates particle size distribution for the pure component ($\beta$-TCP) and the TCP-Silica-Carbamide system from 0.1 µm to 500 µm FIG. 3 graphically illustrates particle size distribution for the pure component ($\beta$-TCP) and the TCP-Silica-Carbamide system from 0.1 µm to 10 µm

For the purposes of promoting an understanding of the principles of the novel technology, reference will now be made to the embodiments illustrated in the drawings and specific language will be used to describe the same. It will nevertheless be understood that no limitation of the scope of the novel technology is thereby intended, such alterations and further modifications in the illustrated device, and such further applications of the principles of the novel technology as illustrated therein being contemplated as would normally occur to one skilled in the art to which the novel technology relates.

Mechanochemical Ball Milling

Mechanochemical (MC) ball milling impacts disparate materials together with sufficient force to form new hybrid or composite materials. These MC milling and hybrid formation processes occur entirely in the solid state, distinguishing MC ball milling from traditional milling. This quasi-destructive process deforms components through powerful collisions between ball-particle, particle-wall, and particle-particle, creating significant grain boundaries at the nanoscale where components have fractured and fused. In order to generate the energy required for such concurrent fracturing and fusion, the vessel containing the balls and material is typically rotated at high speed opposite to the direction of rotation of the platform on which the vessel is placed. These concurrent physical and chemical processes enable the synthesis of hybrid materials having properties and characteristics atypical of materials prepared by the usual synthetic procedures and thus contribute to a myriad of new opportunities. While MC ball milling is typically employed with the goals of reducing particle size and significantly distorting morphological order, the present novel technology uses MC ball milling primarily as a method of chemically blending the individual components while maintaining the morphological and/or property integrity of at least the major substantial component in the material blend. In turn, this allows for tailored and/or improved properties and characteristics of the blended material when used as a component of various formulations.

The current novel technology introduces efficiencies of cost, time, and scale of producing blended materials characterized by specific, predetermined properties without the need for sophisticated chemistries and/or multiple specialized apparatti. The resulting scaleablity may then be realized for applications where localized chemical, mineral or drug delivery is desired.

The novel technology exploits the mechanochemical ball milling process to produce a relatively great amount of relatively inexpensive hybrid materials in a relatively short time. Typically, the hybrid materials are blends of independent organic and inorganic reagents coupled together to yield a blended material characterized by properties similar to those of the starting materials. Typical inorganic materials include minerals (calcium, magnesium, and the like, in oxide form, carbonate form, or the like), clays, rare-earth and metal oxides, or the like, and/or typical organic materials including hydrophilic and hydrophobic molecules, or the like. For example, hybrid silica-carbamide-calcium phosphate systems may be produced in various formulations for improving anti-erosion, remineralization and/or anti-sensitivity efficacy of an oral rinse or paste.

Hybrid Synthesis

An example of a hybrid synthesis from three components is described as follows. β-TCP (~93 wt. %), silica (~5 wt. %), and carbamide (~2 wt. %) are placed into a 500 mL impact vessel containing 20 mm yttria-stabilized zirconium oxide balls. An organic solvent, such as pentane, may be added as lubricant to facilitate blending. The vessel is then capped with a lid, clamped with a bracket, and placed into a loading station with a planetary ball mill (such as a Retsch® PM 400, RETSCH GMBH & CO. KG LIMITED PARTNERSHIP FED REP GERMANY RHELNISCHE STRASSE 36 HAAN FED REP GERMANY 4281). The mill is then actuated for 375 rpm (jar speed is 750 rpm) for 2 hours. After the milling event, the impact vessel was removed from its station and its bracket and lid are removed. The contents are then emptied into a collection pan fitted with a sieve. The pan is then evacuated for several minutes in a vacuum oven (under conditions of 40° C., −28 mm Hg). Afterwards, the pan is removed the contents are weighed and stored in a plastic bottle. The appearance of the blended powder is off-white, fluffy, and soft (cakes easily).

Hybrid Characterization

Infrared spectra and particle size analysis of the blended material and the bulk raw material (β-TCP) were then performed. The IR spectra were collected using an infrared spectrometer and the data is graphically displayed as FIG. 1. The particle size data was collected using a laser diffractor and the results graphically displayed as FIGS. 2 and 3.

Based on the overlapping IR spectra in FIG. 1, the orthophosphate structure of the blended material is largely unchanged relative to the β-TCP raw material. This unexpected result indicates that while a composite material has been synthesized, the structural morphology of the TCP raw material is largely preserved. That this structure would remain intact despite the frequency and intensity of the collisions during the milling process was surprising.

Figure 2:
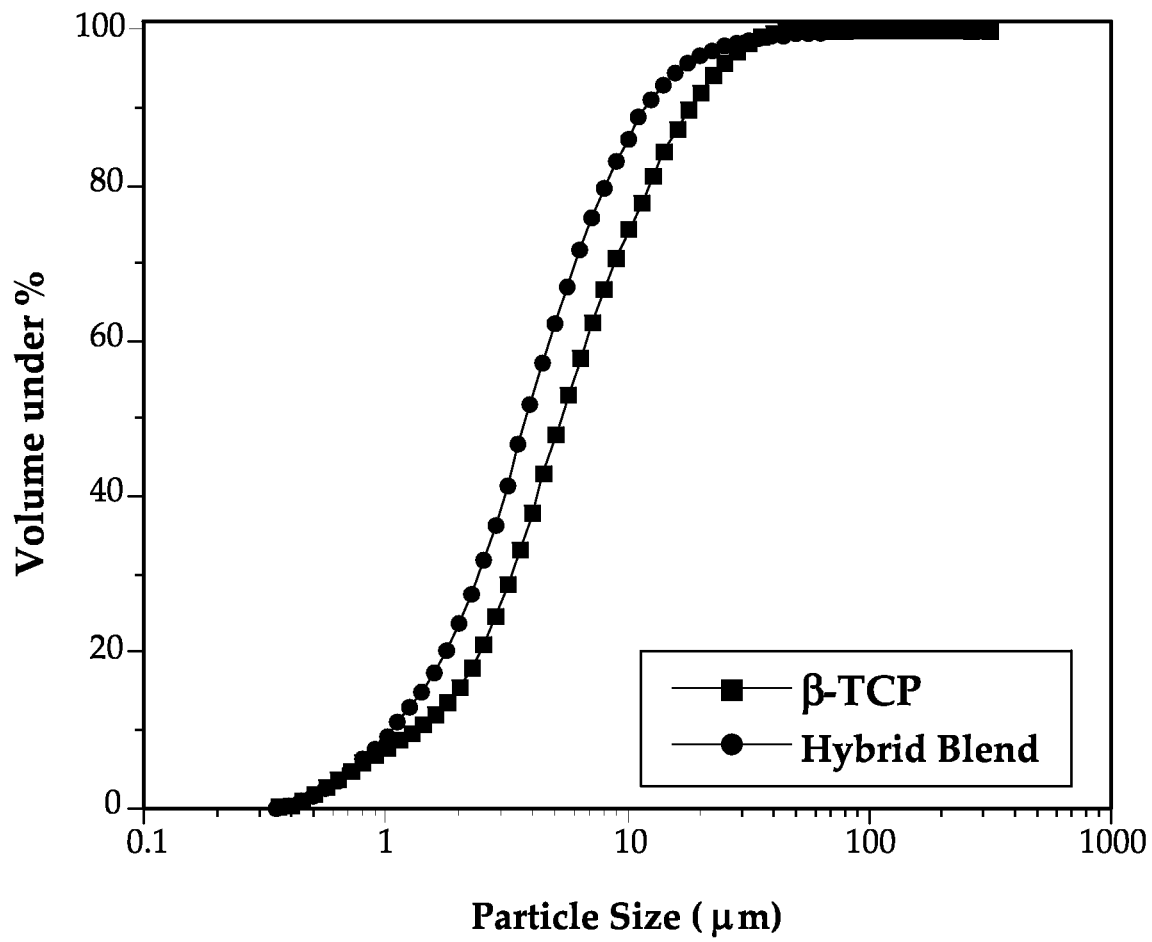
Figure 3:
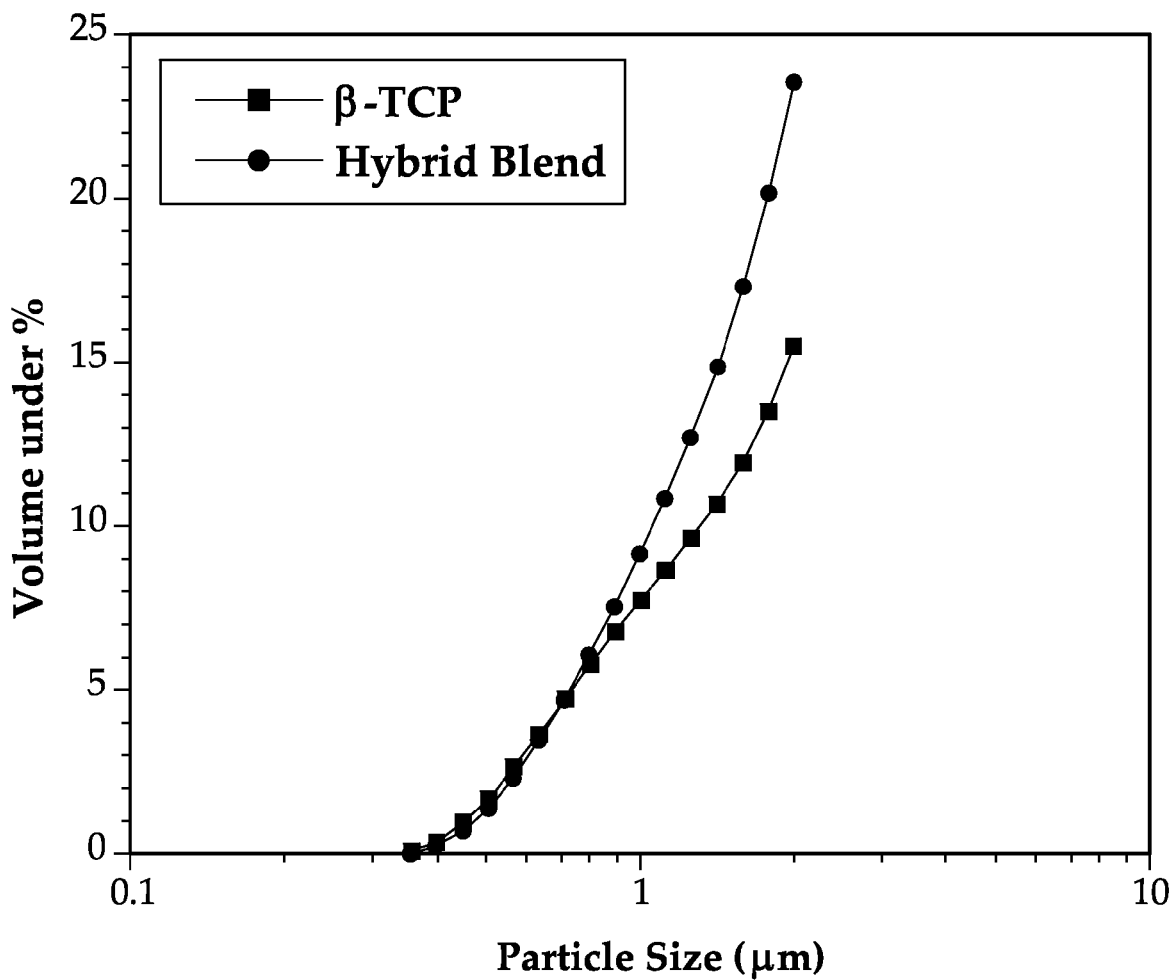

In the cumulative particle size distribution shown in FIG. 2, there is a strong similarity in the particle sizes throughout the size range for both the blended material and the TCP raw material. The blended material particle size is somewhat but not significantly smaller than the raw material particle size within the 1 to 100 micron range. Furthermore, FIG. 3 reveals a narrower range, and, in fact, there appears to be a relatively higher volume fraction of large blended material particles relative to the TCP raw material at particle sizes less than 1 micron.

Thus, the milling procedure produces a hybrid material from the original procedure materials without significantly distorting the morphology of the bulk TCP component. These surprising results clearly contribute to the novelty of the present technology.

Hybrid Efficacy

An efficacy study was run in order to evaluate in multiple pH remin/demin cycling models the efficacy of calcium phosphate blends prepared as described above in remineralizing eroded enamel. These studies involved 226 ppm fluoride rinse systems.

In Vitro Cycling Experiment

The experiment design for the remineralization/demineralization pH cycling study is as follows. Bovine enamel specimens were extracted, ground, and polished. Initial erosion was performed by immersing each enamel specimen in 10 ml of 1% citric acid (pH=3.8) for 30 minutes. After the immersion, four baseline Vickers indentations under a 200 gf load for 15 seconds were made on each specimen and those with a Vickers microhardness number between 200 and 230 VHN were selected for the study. There were three groups in this study (N=10 specimens per group):

Group 1: negative control (DI water)
Group 2: positive control (226 ppm F)
Group 3: 226 ppm F plus 0.004% β-tricalcium phosphate-silica-carbamide The cycling regimen consisted of five, two-minute/day acid challenges and three, two-minute treatments/day. In between treatments and acid challenges, each specimen was immersed in artificial mineral mix. This process was repeated up to 20 days, after which a post-cycle acid challenge was administered using 1% citric acid (pH=3.8) for 11 minutes. The specimens were evaluated for Vickers surface microhardness after 10 and 20 days as well as after the post-cycle acid challenge. The change in Vickers microhardness relative to baseline values was then used as the performance gauge. Remineralization efficacy was evaluated by comparing post surface Vickers microhardness numbers to baseline surface Vickers values. Means and standard deviations of the means were calculated and the Student Q-test was employed to assess accuracy of the individual specimen measurements within each group. Following this, statistical analysis was performed using the Kruskal-Wallis one-way analysis of variance on ranks (ANOVA) to test for the presence of significant differences (p<0.05). If significant differences were found to exist, multiple comparisons of the individual means were then analyzed with the SNK method.

In Vitro Study Results

This cycling study evaluated the β-tricalcium phosphate-silica-carbamide blend when combined in a 226 ppm fluoride (NaF(aq)) solution and tested in a pH cycling model. Surface microhardness measurements were performed after 10 and 20 days of pH cycling, as well as after an 11-minute post-cycle acid challenge) and compared to baseline values as tabulated in TABLE 1. For statistical analyses, a One Way ANOVA was used to determine statistical differences (p<0.05), and the SNK method was used to determine where the differences were. Superscripts indicate significant differences, where 1<2<3.

TABLE 1

| Group # | Mean ΔVHN ± SEM, after 10 days | Mean ΔVHN ± SEM, after 20 days | Mean ΔVHN ± SEM, after post-cycle acid challenge |
| --- | --- | --- | --- |
| 1 | $38.9 \pm 4.8^1$ | $36.7 \pm 5.5^1$ | $46.9 \pm 3.9^1$ |
| 2 | $73.2 \pm 7.0^2$ | $67.6 \pm 7.6^2$ | $81.9 \pm 7.1^2$ |
| 3 | $95.7 \pm 5.8^3$ | $91.1 \pm 7.1^3$ | $116.0 \pm 7.7^3$ |

TABLE. 1 tabulates the anti-erosion efficacy of the TCP-Silica-Carbamide system when added to 226 ppm fluoride relative to fluoride alone After 10 and 20 days of cycling, and after the 11-minute post-cycle acid challenge, the data showed statistical breakage between DI Water and the positive control, indicating model validity (Group 2 >Group 1). At all three measured endpoints, Groups 3 consistently outperformed the other groups. Based on the data above the hybrid blend when combined in a 226 ppm F solution is effective at three different endpoints.

Hybrid Stability with Fluoride

Long-term accelerated aging studies were performed on NaF(aq)-hybrid suspensions. The experiments were carried out in triplicate with 1 mL of each supernatant aspirated, mixed with 1 mL of TISAB II (1:1), and measured with a fluoride-sensitive electrode calibrated to known standards of 100, 950, and 1900 ppm fluoride.

The purpose of this study was to determine if the NaF(aq)-hybrid suspensions maintain sufficient fluoride availability. 0.24% and 0.32% NaF systems were aged for 122 Days @ 40° C.

0.05% NaF systems were aged for 119 Days @ 40° C.

Results

TABLE 2

| NaF(aq)-Hybrid System | Mean ppm F ± Std. Dev | % Relative to Control |
| --- | --- | --- |
| 0.24% NaF Control | 1080.7 ± 4.8 | N/A |
| 0.24% NaF + 0.04% Hybrid | 1039.9 ± 2.3 | -3.8% |
| 0.32% NaF Control | 1493.3 ± 3.3 | N/A |
| 0.32% NaF + 0.04% Hybrid | 1416.8 ± 3.1 | -5.1% |
| 0.05% NaF Control | 231.7 ± 0.5 | N/A |
| 0.05% NaF + 0.004% Hybrid | 225.8 ± 0.5 | -2.5% |

TABLE. 2 tabulates the fluoride compatibility of the TCP-Silica-Carbamide system when added to 226 ppm fluoride relative to fluoride alone after 122 and 119 days accelerated aging at @ 40° C.

Based on the data above, the β-tricalcium phosphate-silica-carbamide hybrid system demonstrates sufficient fluoride availability (within 10%) relative to the control systems.

While the novel technology has been illustrated and described in detail in the drawings and foregoing description, the same is to be considered as illustrative and not restrictive in character, it being understood that only the preferred embodiment has been shown and described and that all changes and modifications that come within the spirit of the novel technology are desired to be protected.

What is claimed:

1. A chemical composition, comprising:
   a hybrid calcium phosphate material, made by milling together the following components:
   crystalline β-tricalcium phosphate;
   at least one metal oxide; and
   at least one organic compound;
   wherein the β-tricalcium phosphate, the at least one metal oxide and the at least one organic compound are fused together to produce said hybrid calcium phosphate material; and
   wherein the crystalline structure of the β-tricalcium phosphate is substantially intact; and
   a dental formulation;
   wherein the hybrid calcium phosphate material remineralizes teeth that have been damaged by members selected from the group consisting of dental erosion and wear, caries, hypersensitivity, and combinations thereof.

2. The chemical composition of claim 1 wherein fluoride is absent.

3. The chemical composition of claim 1 wherein fluoride is present in the form of a single aqueous formulation and wherein fluoride remains available during storage.

4. The chemical composition of claim 1 wherein the dental formulation is selected from the group including pastes, rinses, gels and combinations thereof.

5. A dental formulation, comprising:
   fluoride; and
   a hybrid calcium phosphate material, made by milling together the following components:
   crystalline β-tricalcium phosphate;
   at least one metal oxide; and
   at least one organic compound;
   wherein the β-tricalcium phosphate, the at least one metal oxide and the at least one organic compound are fused together to produce said hybrid calcium phosphate material; and
   wherein the crystalline structure of the β-tricalcium phosphate is substantially intact; and
   wherein in an oral environment, the hybrid calcium phosphate material of the dental formulation remineralizes teeth.

6. A dental application material, comprising:
   a dental delivery medium selected from the group consisting of pastes, rinses, gels and combinations thereof;
   fluoride; and
   a hybrid calcium phosphate material made by milling together the following components:
   crystalline β-tricalcium phosphate;
   at least one metal oxide selected from the group consisting of silica, magnesia, iron oxide, and combinations thereof; and at least one organic compound selected from the group consisting of ureas, amides, carbamide and combinations thereof;

wherein the β-tricalcium phosphate, the at least one metal oxide and the at least one organic compound are fused together to produce said hybrid calcium phosphate material; and wherein the crystalline structure of the β-tricalcium phosphate is substantially intact;

wherein the β-tricalcium phosphate is present in an amount between about 50 and about 98 weight percent;

wherein the at least one metal oxide is present in an amount between about 0.1 and about 50 weight percent; and wherein the organic compound is present in an amount between about 0.1 and about 90 weight percent.

7. The dental application material of claim 6 wherein in an oral environment, the hybrid calcium phosphate material of the dental formulation remineralizes teeth.

* * * * *